United States Patent [19]

Ideker et al.

[11] Patent Number: 5,224,476
[45] Date of Patent: Jul. 6, 1993

[54] METHOD AND APPARATUS FOR CONTROLLING FIBRILLATION OR TACHYCARDIA

[75] Inventors: Raymond E. Ideker; Paul A. Guse, Durham, both of N.C.

[73] Assignee: Duke University, Durham, N.C.

[21] Appl. No.: 840,387

[22] Filed: Feb. 24, 1992

[51] Int. Cl.$^5$ .............................................. A61N 1/39
[52] U.S. Cl. ...................... 128/419 D; 128/419 PG
[58] Field of Search ................... 128/419 D, 783, 784, 128/785, 786, 421, 419 PG, 419 P, 702, 705

[56] References Cited

U.S. PATENT DOCUMENTS

| | | | |
|---|---|---|---|
| 4,850,357 | 7/1989 | Bach, Jr. ........................ | 128/419 D |
| 4,953,551 | 9/1990 | Mehra et al. .................... | 128/419 D |
| 5,083,562 | 1/1992 | de Coriolis et al. ............ | 128/419 D |
| 5,099,838 | 3/1992 | Bardy ............................... | 128/419 D |

Primary Examiner—Kyle L. Howell
Assistant Examiner—George Manuel
Attorney, Agent, or Firm—Bell, Seltzer, Park & Gibson

[57] ABSTRACT

A method and apparatus for delivering a waveform, including a predetermined series of electrical pulses, to the heart by electrodes positioned adjacent the heart. In a first embodiment of the invention, a series of four electrical pulses are delivered from an electrical pulse generator including a charged storage capacitor through two pairs of electrodes and define a waveform comprising two interleaved biphasic signals. The series of electrical pulses have a low defibrillation threshold and require a relatively small amount of energy.

In a second embodiment of the invention, a triphasic waveform is applied to the heart through four electrodes. One of the pulses in the triphasic waveform is generated by all four electrodes and in a polarity opposite that of the other two pulses. The pulse generated by all four electrodes may be applied first, second, or third in the series of electrical pulses.

34 Claims, 3 Drawing Sheets

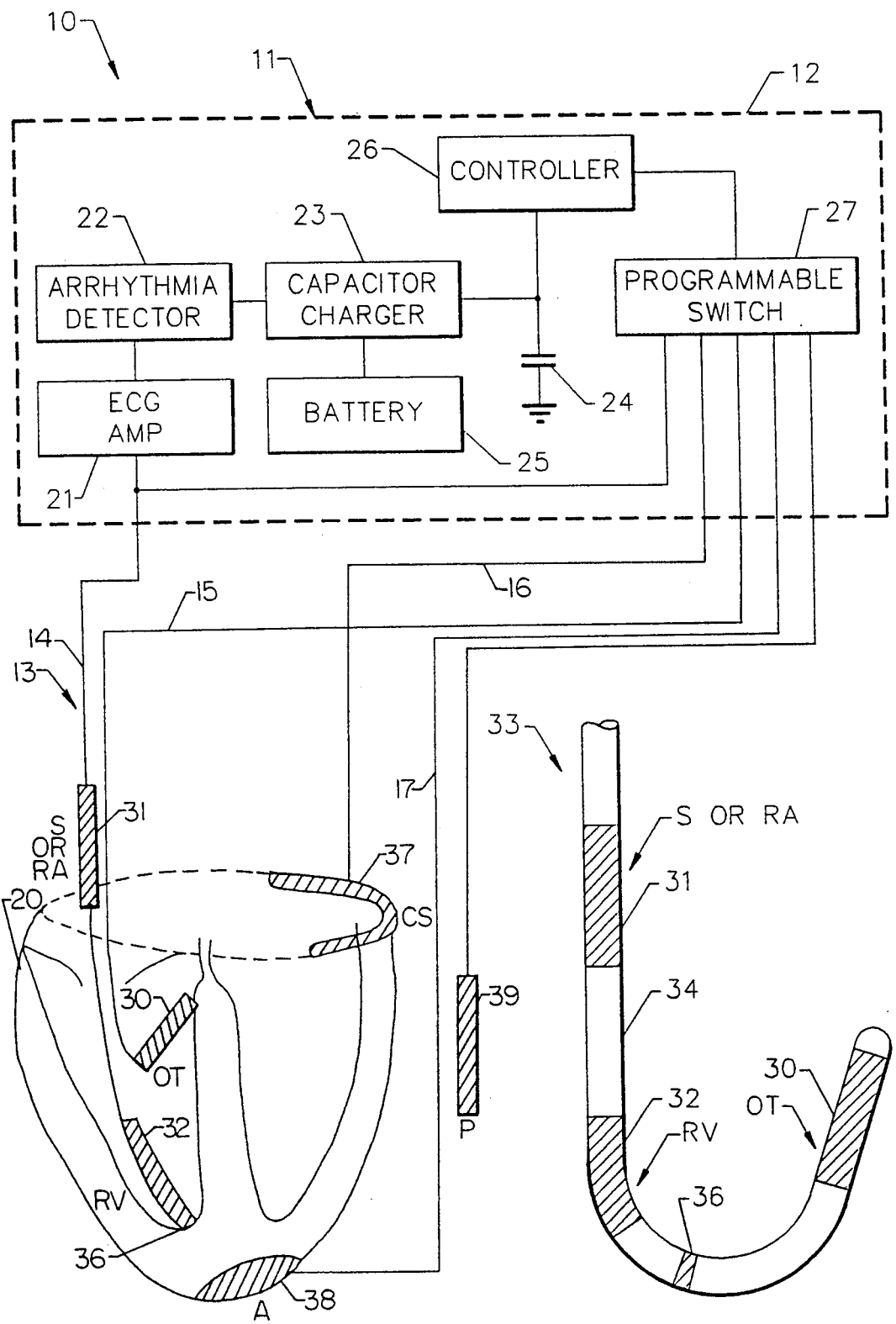

ic pulse is delivered by the first pair of electrodes in a polarity opposite the predetermined polarity of the first electrical pulse; and the fourth electrical pulse is delivered by the second pair of electrodes in a polarity opposite the predetermined polarity of the second electrical pulse.

METHOD AND APPARATUS FOR CONTROLLING FIBRILLATION OR TACHYCARDIA

This invention was made with government support under grant number HL-42760 awarded by the National Institutes of Health. The government has certain rights to this invention.

FIELD OF THE INVENTION

The invention relates to the field of defibrillation, and more particularly, to a method and an apparatus for controlling fibrillation or tachycardia by delivering a waveform to the heart including a predetermined sequence of electrical pulses.

BACKGROUND OF THE INVENTION

It is known that ventricular fibrillation, an often fatal heart arrhythmia, can be terminated by the application of one or more electrical current pulses delivered to the heart through electrodes applied to the chest or implanted within the body. Since the first use on humans of a completely implantable cardiac defibrillator in 1980, research has focussed on making continually smaller and more efficient defibrillation devices. In addition, reducing the defibrillation threshold (DFT) energy level applied to the heart by the defibrillation pulses reduces the likelihood of damaging tissue adjacent the electrodes.

A conventional implantable defibrillator includes an electrical pulse generator and an arrhythmia detection circuit coupled to the heart by a series of two or more electrodes implanted in the body. A battery power supply, and one or more charge storage capacitors are used for delivering defibrillation shocks in the form of electrical current pulses to the heart.

Currently, the primary constraint in reducing the size of an implantable defibrillator is reducing the battery size and the size of the storage capacitor(s). Accordingly, improvements in the area of implantable defibrillators have focussed in two areas: (1) more efficient defibrillation waveforms, and (2) more efficient electrode configurations and placements. Stated in other words, the primary variables that can be adjusted in the design to lower the shock strength required for defibrillation include those variables relating to the defibrillation waveform, such as duration, polarity, and waveshape, and those variables relating to the electrodes, such as materials, size, shape, and location.

An example of a development in the area of electrodes is U.S. Pat. No. 4,827,932 to Ideker et al. which relates to a pair of spaced apart epicardial implantable defibrillation patch electrodes. A respective patch electrode is attached over each of the right and left ventricles in an attempt to achieve a uniform voltage gradient throughout the entire ventricular mass.

In the area of defibrillation waveforms, U.S. Pat. No. 4,641,656 to Smits discloses a method of applying a sequence of defibrillating pulses to the heart from a series of four electrodes. Two adjacent electrodes have positive polarity and the other two electrodes have negative polarity in an attempt to concentrate defibrillation energy in the heart wall rather than through the center of the heart. Two or more such pulses are applied, with a reverse in polarity of one pair of opposing electrodes between each pulse. Another pulsing scheme is disclosed wherein the polarity of the four electrodes alternates with each adjacent electrode, and with all four electrodes used simultaneously to defibrillate the heart.

A publication abstract entitled *New Waveforms and Defibrillation in Pigs: Biphasic, Sequential & Biphasic Sequential*, by Jones et al. appearing in Proceedings AAMI, 25 Annual Meeting and Exposition, May 5-9, 1990, discloses several defibrillation waveforms delivered using an orthogonal four-patch electrode combination. An individual storage capacitor is provided to generate each of four pulses delivered to the heart. The results of the study described in the abstract provided that using two opposing electrodes and a biphasic pulse required the highest energy, that a sequential pulse using all four electrodes was intermediate, that the combination of the biphasic and sequential pulses provided a lower threshold, and that altering the order of pulses influenced the threshold with an orientation of one biphasic pathway followed by the second biphasic pathway being less efficacious than two sequential pulses of opposite polarity. Unfortunately, an implantable device having four capacitors, and the required charging and control circuitry for each of the four capacitors, would be relatively physically large and energy inefficient because of the residual charge remaining in each of the capacitors.

Other examples of defibrillating waveforms are disclosed in U.S. Pat. No. 4,637,397 to Jones et al., U.S. Pat. No. 4,800,883 to Winstrom, and U.S. Pat. No. 4,821,723 to Baker, Jr. et al. These patents disclose multiphasic defibrillation waveforms wherein the polarity of pulses is reversed. U.S. Pat. No. 4,768,512 to Imran relates to a high frequency truncated exponential waveform. U.S. Pat. No. 4,727,877 to Kallok discloses a transvenous lead configuration wherein a first electrical pulse is delivered to a first pair of electrodes between the right ventricular apex and the superior vena cava, and after a predetermined delay, a second pulse is delivered to a second pair of electrodes between the right ventricular apex and the coronary sinus.

Despite improvements in the art of waveforms for controlling fibrillation or tachycardia, there still exists a need to increase the energy efficiency of such waveforms while also reducing the likelihood of damage to tissue adjacent the implanted electrodes.

SUMMARY OF THE INVENTION

It is therefore an object of the present invention to provide a method and an apparatus for controlling fibrillation or tachycardia in a heart that provides efficient use of energy.

It is another object of the present invention to provide a method and an apparatus for controlling defibrillation or tachycardia in a heart which minimizes the energy delivered to the heart to thereby reduce the likelihood of tissue damage adjacent the electrodes.

These and other objects and advantages are provided by a first embodiment of the method according to the present invention which includes the steps of positioning a first pair of opposing electrodes and a second pair of opposing electrodes adjacent predetermined portions of the heart, charging a storage capacitor and delivering a series of four electrical pulses to the heart from the thus charged storage capacitor wherein the four electrical pulses define two interleaved biphasic signals. In other words, a first electrical pulse is delivered by the first pair of electrodes in a predetermined polarity; the second electrical pulse is delivered by the second pair of electrodes in a predetermined polarity; the third electrical pulse is delivered by the first pair of electrodes in the opposite polarity to the first pulse; and the fourth electrical pulse is delivered by the second pair of electrodes in the opposite polarity to the second pulse. Thus, the first and third pulses define a first biphasic signal to the first pair of electrodes and the second and the fourth pulses to the second pair of electrodes define a second biphasic signal thereby producing a waveform comprising two interleaved biphasic signals.

The waveform efficiently utilizes energy stored in the capacitor. The waveform is compatible with the decaying voltage available from the capacitor as it is successively discharged by the series of pulses. Accordingly, a single capacitor, or bank of parallelled capacitors, may thus be used with relatively simple control electronics for charging and controlling the discharge of the capacitor.

It has been found, according to one aspect of the invention, that the efficacy of two biphasic electrical pulses separated by an amount of time not greater than about 6 milliseconds (ms) is substantially the same as the efficacy where the two biphasic pulses are consecutive, that is, the second pulse immediately follows the first pulse. Accordingly, two biphasic signals may be interleaved. Since the series of electrical pulses is provided by a decaying voltage source, that is, the charged capacitor, interleaving the biphasic signals permits a higher voltage to be available for the initial pulse of the second biphasic signal than would be available in a sequential biphasic waveform where the second biphasic signal would comprises the third and fourth pulses in the series. It has also been found that each of the first through the fourth electrical pulses according to the invention is preferably delivered for a time period in the range of about 2 ms to 6 ms.

The first and second pairs of electrodes are preferably positioned so that each pair produces a relatively high current flow in regions of the heart where the other pair produces a relatively low current flow. The first pair of electrodes preferably comprises a first catheter electrode in the right ventricle and a second subcutaneous patch electrode on the left thorax, and the second pair of electrodes preferably comprises a third catheter electrode in the superior vena cava and a fourth patch electrode on the left ventricular apex. As would be readily understood by those skilled in the art, other electrode configurations and placements are also possible. For example, an electrode may be positioned in the right ventricular outflow tract rather than the superior vena cava, and an electrode may be positioned in the coronary sinus rather than subcutaneously on the left thorax. In addition, an electrode may comprise two or more electrical conductors connected in parallel.

A second embodiment of the method according to the invention comprises delivering a triphasic waveform to the heart wherein one of the phases (pulses) is delivered by a combination of the electrodes. A series of four electrodes are positioned adjacent predetermined portions of the heart, a first and a second electrode in opposing relation and defining a first electrode pair, and a third and a fourth electrode in opposing relation and defining a second electrode pair. A series of three electrical pulses are delivered to the heart. Two of the electrical pulses are delivered by the first electrode pair in a predetermined polarity and by the second electrode pair in a predetermined polarity, respectively. The other electrical pulse is delivered by the first and third electrodes jointly and the second and fourth electrodes jointly in a polarity opposite the respective predetermined polarities of the two electrical pulses delivered by the first and second electrode pairs.

The combination electrical pulse delivered by the first and third electrodes jointly and the second and fourth electrodes jointly may be performed first, second, or third in the series of three electrical pulses. As in the first embodiment of the method according to the invention, the series of three electrical pulses to the heart is preferably delivered from a decaying voltage source, such as an electrically charged capacitor having a single charge stored therein. The electrodes are also preferably positioned as described above for the first embodiment according to the invention.

A first embodiment of the implantable apparatus for controlling ventricular fibrillation or tachycardia in a heart according to the present invention includes first and second pairs of opposing electrodes adapted to be positioned adjacent predetermined portions of the heart, and an electrical pulse generator coupled to the electrodes for delivering a series of four electrical pulses (two interleaved biphasic signals) to the heart as described above with respect to the first embodiment of the method according to the invention.

The electrical pulse generator includes a controllable or programmable switch or other means for controlling the duration of each pulse, the time delay between successive pulses, and to which pair or pairs of electrodes each pulse is delivered. Preferably the leading edge of the third pulse is delivered not greater than 6 ms from the trailing edge of the first pulse and the leading edge of the fourth pulse is delivered not greater than about 6 ms from the trailing edge of the second pulse. The time duration of each pulse is also preferably within the range of about 2 ms to 6 ms.

The electrical pulse generator also preferably includes a storage capacitor for storing a single charge therein and thereby provides a decaying voltage source for the series of four electrical pulses. A battery power supply provides the electrical energy for charging the capacitor. A conventional arrhythmia detector well known to those skilled in the art, monitors the heart and triggers activation of the electrical pulse generator to thereby deliver the series of four electrical pulses to the heart.

The second embodiment of the apparatus according to the invention includes a first pair of opposing electrodes and a second pair of opposing electrodes adapted to be positioned adjacent predetermined portions of the heart. The first pair of electrodes includes first and second electrodes, and the second pair of electrodes includes third and fourth electrodes. An electrical pulse generator is coupled to the first and second pairs of electrodes for delivering a series of three electrical pulses to the heart, that is, a triphasic signal wherein one of the phases is delivered by a combination of electrodes. Two of the electrical pulses are for delivery by the first electrode pair in a predetermined polarity and by the second electrode pair in a predetermined polarity, respectively. The other electrical pulse is for delivery by the first and third electrodes jointly and the second and fourth electrodes jointly in a polarity opposite the respective predetermined polarities of the two electrical pulses for delivery by the first and second electrode pairs.

The electrical pulse generator in the second embodiment of the apparatus according to the invention includes a controllable or programmable switch or other means for delivering the combined electrode electrical pulse first, second, or third in the series of three electrical pulses. The controllable switch also preferably controls the time duration of each electrical pulse within the range of about 2 ms to 6 ms. A capacitor and associated battery provide the energy supply for the electrical pulses. A conventional arrhythmia detector triggers application of the three electrical pulses.

The two waveform embodiments according to the invention provide a number of advantages. Because energy is more efficiently used, the size of the battery supply or storage capacitor may be reduced over that for conventional waveforms, such as a series of monophasic electrical pulses. Alternately, for a given size battery and capacitor, the effective life of the implantable apparatus may be extended. In addition, a lowered defibrillation threshold (DFT), that is, a lower leading edge voltage of the initial pulse may be used to thereby reduce the possibility of causing damage to adjacent portions of the heart or to reduce the possibility of refibrillating the heart. The lower leading edge voltage may also permit a quicker charging time for the capacitor, thereby providing a quicker application of the defibrillation waveform to the patient.

BRIEF DESCRIPTION OF THE DRAWINGS

FIG. 1 is a schematic diagram illustrating the apparatus for controlling fibrillation or tachycardia in a heart according to the present invention.

FIG. 2 is schematic view of an intravascular catheter supporting a series of electrodes as used in the apparatus shown in FIG. 1.

DETAILED DESCRIPTION OF THE PREFERRED EMBODIMENTS

Figure 3:
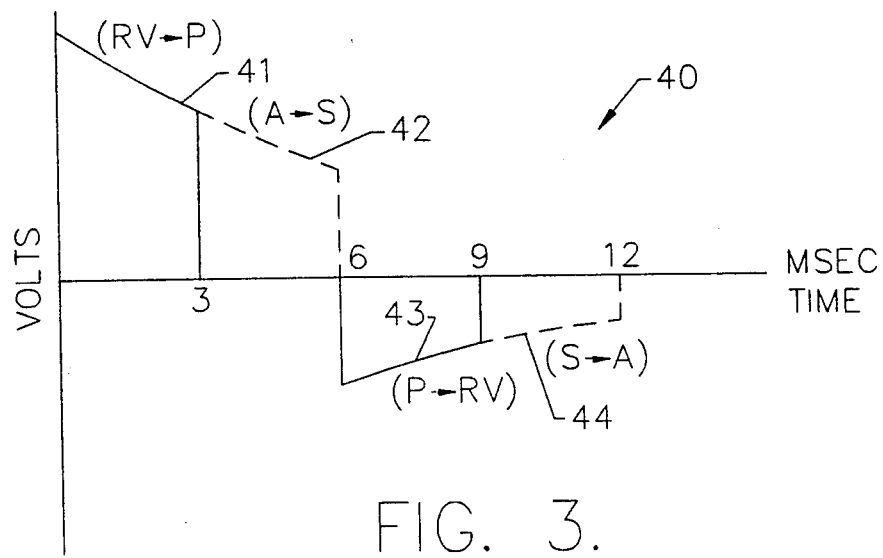
FIG. 3 is a schematic representation of a waveform to be applied by the apparatus shown in FIG. 1 according to a first embodiment of the method of the invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, applicants provide these embodiments so that this disclosure will be thorough and complete, and will fully convey the scope of the invention to those skilled in the art.

As shown in the schematic diagram of FIG. 1, the implantable apparatus 10 for controlling fibrillation or tachycardia according to the present invention includes an electronic circuit 11 contained within an implantable housing 12. The electronic circuit 11 is connected by a series of leads 14, 15, 16, 17 and 18 to an electrode configuration 13 including a series of electrodes positioned adjacent predetermined portions of the heart 20, as described in greater detail below.

The electronic circuit 11 includes a conventional ECG amplifier 21 for amplifying sensed cardiac signals. The amplified cardiac signals are analyzed by a conventional arrhythmia detector 22 which determines if and what type of arrhythmia is present. The arrhythmia detector 22 may be one of several types well known to those skilled in the art and is preferably capable of distinguishing between high rate malignant tachycardias and ventricular fibrillation so as to deliver lower energy shocks in the former case than those to be delivered in the latter case.

A capacitor charging circuit 23, in response to a signal from the arrhythmia detector 22, charges the storage capacitor 24 to a predetermined voltage from the battery 25. The voltage may selected prior to implantation of the apparatus 10. The discharge of the capacitor 24 is controlled by the controller 26, or multi-phasic circuit, such as described in U.S. Pat. No. 4,850,357. The capacitor 24 may be a single capacitor or a bank of parallel connected capacitors of equivalent capacity as would be readily understood by those skilled in the art.

The controller 26 delivers a series of electrical pulses to predetermined ones of the electrodes through a programmable switch 27. As would be readily understood by those skilled in the art, the voltage waveform delivered by the capacitor 24 is a decaying exponential waveform. The capacitor charger 23, capacitor 24, battery 25, controller 26 and programmable switch 27 thus form an electrical pulse generator for the apparatus 10.

The electrode configuration 13 is preferably a substantially non-thoracotomy multi-electrode configuration or multiple single electrode configuration as known to those skilled in the art. In the illustrated embodiment, four catheter mounted electrodes are shown, one catheter supporting a distal electrode 30 positioned in the right ventricular outflow tract (OT), a proximal electrode 31 positioned in the superior vena cava (S) or the right atrium (RA) (not shown), and an intermediate electrode 32 positioned in the right ventricular apex (RV).

As shown in FIG. 2, the S (or RA) electrode 31, the RV electrode 32, and the OT electrode 30 may be supported on a single J-shaped intravascular catheter. Each of the electrodes 31, 32, 30 is connected to respective leads, shown schematically in FIG. 1, extending through the catheter body 34. In addition, a sensing ring electrode 36 is provided adjacent the distal end of the catheter 33 for sensing the electrical activity of the heart 20 for input to the ECG amplifier 21 and arrhythmia detector 22 (FIG. 1).

A lead 16 extends into and supports an electrode 37 in the coronary sinus (CS). This lead 16 may be a small diameter single chamber defibrillation catheter lead without a pacing tip as would be readily understood by those skilled in the art. The non-catheter supported electrodes may include one or both of an apical patch electrode 38 mounted adjacent the left ventricular apex (A), and a subcutaneous patch electrode 39 positioned beneath the skin outside the left portion of the thoracic cavity (P).

Electrode placement may preferably be determined in the laboratory by mapping studies which are representative of the overall patient population. Such generalized mapping studies are performed to determine typical voltage gradients across predetermined portions of the myocardium in response to various electrode placement configurations. (See, for example "Measurement of Defibrillation Shock Potential Distributions and Activation Sequences of the Heart in Three Dimensions" by Tang et al. and published in the Proceedings of the IEEE, Vol. 76, pp. 1176–1186, 1988). Recording electrodes are inserted into the atria, ventricles and intraventricular septum to record from many sites throughout the heart. An electrical shock or pulse is delivered by a pair of electrodes and signals are recorded. Computer assisted mapping may then be used and localized potential gradients calculated. (See, for example "Computer Techniques for Epicardial and Endocardial Mapping", by Smith et al. appearing in Progress of Cardiovascular Discovery, Vol. 26, pp. 15–32, 1983, and "Measured and Calculated Epicardial Potentials and Gradients Resulting from Transthoracic Stimulation", by Clayton in his 1987 Ph.D. Dissertation, from Duke University in Durham, N.C.).

The mapping studies are performed on representative patients or animals to determine, on average, the localized high and low voltage gradient regions. Accordingly, a feature of the present invention is that first and second pair of electrodes may be advantageously implanted adjacent the heart wherein one pair produces a relatively high potential gradient in regions where the other pair produces a relatively low potential gradient and vice versa.

A first embodiment of the method according to the present invention may best be understood with reference to FIG. 3 which illustrates a voltage waveform 40 with respect to time as applied to the electrodes as indicated. A series of four electrical pulses 41–44 are delivered to predetermined areas of the heart. A first electrical pulse 41 is delivered by the first pair of electrodes in a predetermined polarity, such as RV→P, where the arrow (→) indicates that RV is the cathode and P is the anode. A second electrical pulse 42 is delivered by the second pair of electrodes in a predetermined polarity (A→S). A third electrical pulse 43 is then delivered again by the first pair of electrodes, but in the opposite polarity to the first pulse, that is, the third pulse is delivered P→RV. The fourth electrical pulse 44 is delivered again by the second pair of electrodes and in the opposite polarity to the second pulse, that is, S→A.

The position of the pulses 43, 44 as shown in FIG. 3 above or below the abscissa are intended to highlight that the relative pulse polarities are reversed for each phase of a biphasic signal; however, it would be readily understood by those skilled in the art that the notations within parentheses, for example (RV→P) followed by the reversal (P→RV), redundantly convey this same polarity reversal. It would also be readily understood by those skilled in the art, that other electrode configurations may be used to generate the interleaved biphasic signals comprising the waveform 40 shown in FIG. 3. For example, an OT electrode 30 (FIG. 1) may be used in place of the S electrode 31, and/or a CS electrode 37 (FIG. 1) may be used in place of the P electrode 39. The order of the pulses may also be varied as long as the waveform represents two interleaved biphasic signals.

Although the duration of each pulse 41–44 in the illustrated waveform 40 is 3 ms, other pulse durations may also be used and a time delay may be inserted between adjacent pulses. However, it is preferred that for a given pair of electrodes, that the leading edge of the second pulse follows within about 6 ms of the trailing edge of the first pulse from that given pair of electrodes. It has been determined that a delay between the two opposite polarity pulses defining a biphasic signal can be as high up to about 6 ms without reducing the efficacy of the defibrillation, in terms of the DFT and the total energy of the waveform, over that obtained by two consecutive opposite polarity pulses.

Each of the electrical pulses 41–44 is also preferably delivered for a time period in the range of about 2 ms to 6 ms. The series of four electrical pulses 41–44 may preferably be supplied by a decaying exponential voltage source of the type delivered from a charged capacitor 24 (FIG. 1). The use of a single charge storage capacitor, or parallel connected bank of capacitors of equivalent capacity, permits reduction of the size of the overall device, or may permit a larger battery size and longer life for the device.

Figure 4:
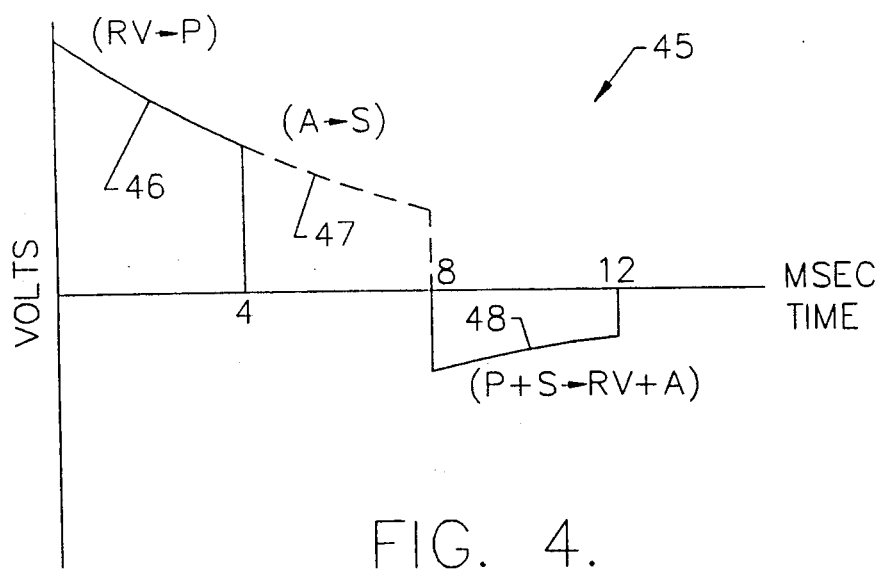
FIGS. 4–6 are schematic representations of three variations of waveforms to be applied by the apparatus shown in FIG. 1 according to a second embodiment of the method of the invention.
Figure 5:
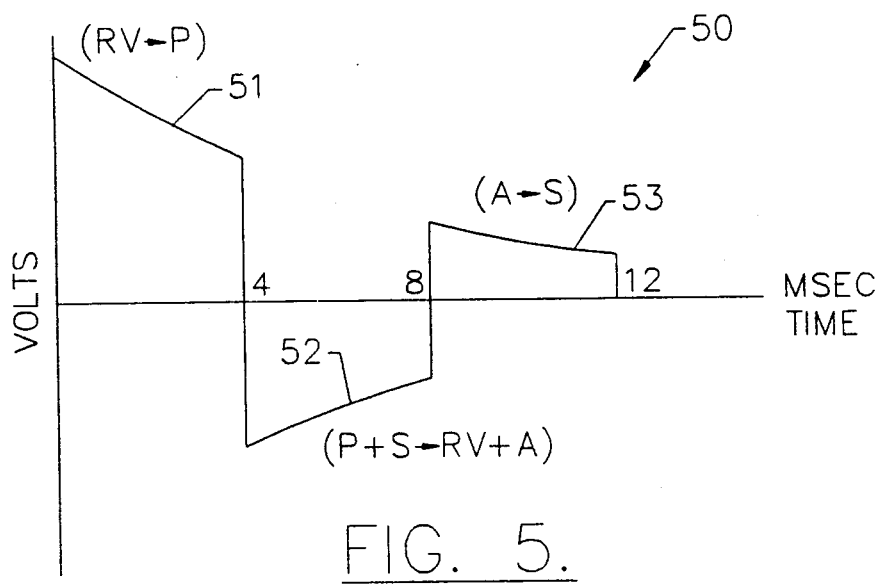
Figure 6:
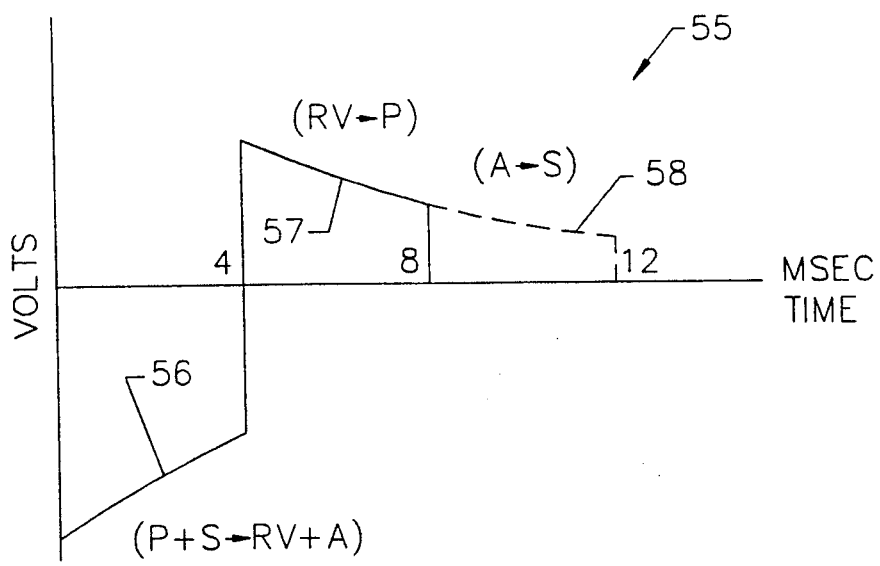

FIGS. 4–6 illustrate the three variations of waveforms 45, 50, 55 for a second embodiment of the method according to the invention. In this embodiment, a triphasic waveform is used wherein one of the pulses is delivered by simultaneous, or overlapping, operation of both pairs of electrodes. FIG. 4 shows a waveform 45 wherein the third electrical pulse 48 is the combined pulse delivered in the series of three electrical pulses. More particularly, the first pulse 46 and the second pulse 47 are delivered by the first electrode pair (RV→P) in a predetermined polarity and by the second electrode pair (A→S) in a predetermined polarity, respectively. The third pulse 48 is delivered by the first and third electrodes jointly and the second and fourth electrodes jointly in a polarity opposite the respective predetermined polarities of the two electrical pulses delivered by the first and second electrode pairs, that is, P+S→RV+A.

In a similar fashion, FIG. 5 illustrates a triphasic waveform 50 wherein the combined electrode pulse is the second pulse 52 in the series of three pulses 51–53. FIG. 6 illustrates variation of a triphasic waveform 55 wherein the combined electrode pulse is the first pulse 56 in the series of three pulses 56–58.

As noted above in the description of FIG. 3, the position of the pulses shown in FIGS. 4–6 above or below the abscissa are intended to highlight that the relative pulse polarities are reversed as described; however, it would be readily understood by those skilled in the art that the notations within parentheses redundantly convey this same polarity reversal. It would also be readily understood by those skilled in the art, that other electrode configurations may be used to generate the waveforms 45, 50 55. For example, an OT electrode 30 (FIG. 1) may be used in place of the S electrode 31, and/or a CS electrode 37 (FIG. 1) may be used in place of the P electrode 39.

As illustrated in FIGS. 4–6, each of the series of three pulses may be consecutive and have a duration of about 4 ms. It is preferred that the duration of each pulse be in the range of about 2 ms to 6 ms.

Returning again to the apparatus 10 according to the present invention, the controller 26 in combination with the programmable or controllable switch 27 may be configured to provide any of the waveforms 40, 45, 50, 55 described and as illustrated in FIGS. 3–6 with respect to the embodiments of the method according to the invention.

The following Examples are further illustrative of the invention and are not intended to be limiting of the scope of the invention.

EXAMPLE 1

In this Example, the waveform 40 as shown in FIG. 3 having a series of four pulses was evaluated. Defibrillation catheters were placed in the right ventricle (RV) and the superior vena cava (S) of six pigs. A small patch electrode (4.2 cm$^2$) was sutured to the left ventricular apex (A) and a 42 cm$^2$ R2 cutaneous patch electrode (P) was placed on the left thorax. R2 is a trademark of the Darox Corp. of Niles, Ill. and the model used was the Model 412.

This Example tested the efficacy of the interleaved biphasic waveform 40 compared to the efficacy of sequential monophasic shocks. TABLE 1 below shows the results of comparing the interleaved biphasic waveform 40 in which each pulse was 3 ms as shown in FIG. 3; and a sequential monophasic waveform, not shown, in which a 6 ms monophasic pulse was delivered by a first pair of electrodes (RV→P), followed by a second 6 ms pulse delivered by a second pair of electrodes (A→S). Both of the waveforms were generated from a single capacitor defibrillator. Using a modified Purdue technique, DFT's were determined with shock steps of 20 volts and expressed as leading edge voltage and total energy (J) ±SEM. (*=P<0.001 for the interleaved biphasic waveform versus the sequential monophasic).

TABLE 1

|  | Interleaved Biphasic | Sequential Monophasic |
|---|---|---|
| Volts | 256 ± 14* | 370 ± 18 |
| Joules | 4.8 ± 0.5* | 10.6 ± 1.0 |

As shown in TABLE 1, the interleaved biphasic waveform required a substantially lower voltage as well as a substantially lower total energy compared to the sequential monophasic waveform.

EXAMPLE 2

In this Example, the triphasic waveform 45 as shown in FIG. 4 having a series of three pulses was evaluated. In 6 pigs, defibrillation catheters were placed in the right ventricle (RV) and the superior vena cava (S). A stainless steel patch electrode (4.2 cm$^2$) was sutured to the left ventricular apex (A) and a 42 cm$^2$ R2 cutaneous patch electrode (P) was placed on the left thorax.

This Example tested the efficacy of the triphasic waveform 45 as shown in FIG. 4, over a single biphasic waveform, not shown. TABLE 2 below shows the DFT's and total energy for the triphasic waveform 45 in which a 4 ms pulse was delivered to RV→P, then a 4 ms pulse delivered to A→S, and finally a 4 ms pulse was delivered to P+S→RV+A; and a single biphasic waveform in which a first 6 ms pulse was delivered in a first polarity to RV→P+S followed by a second 6 ms pulse in the opposite polarity. All waveforms were generated from a single capacitor defibrillator connected to customized switches. DFT's were determined with shock steps of 20 volts using a modified Purdue technique and expressed as leading edge voltage and total energy (J) ±SEM. (*=P<0.001 for versus the biphasic).

TABLE 2

|  | Triphasic | Biphasic |
|---|---|---|
| Volts | 253 ± 16* | 324 ± 18.0 |
| Joules | 5.0 ± 0.7* | 9.0 ± 1.0 |

The triphasic waveform used required a substantially lower voltage, as well as a lower total energy compared to the biphasic waveform.

EXAMPLE 3

This Example tested the efficacy of the three triphasic waveforms 45, 50, 55 in shown in FIGS. 4-6. In 9 pigs, defibrillation catheters were placed in the right ventricle (RV) and the superior vena cava (S). A mesh electrode (4.2 cm$^2$) was sutured to the left ventricular apex (A) and a 42 cm$^2$ R2 cutaneous patch electrode (P) was placed on the left thorax.

In addition to the waveforms shown in FIGS. 4-6, a slight variation based upon the waveform of FIG. 4 (identified in the TABLE 4 as FIG. 4*) was also tested. In addition to the waveforms according to the invention, a triphasic waveform (TM) was tested in which all phases were 4 ms and were monophasic, that is, there was no reversal of polarity. All waveforms were generated from a single capacitor defibrillator. DFT's were determined using an up/down technique, and expressed as total energy ±SEM. (*=P<0.0001 for the waveforms according to the invention compared to the TM waveform).

TABLE 3

| Waveform | 1st Phase | 2nd Phase | 3rd Phase | Joules* | Volts* |
|---|---|---|---|---|---|
| FIG. 4 | RV → P | A → S | P + S → RV + A | 6.0 ± 0.4 | 283 ± 8 |
| FIG. 4M | RV → P | S → A | P + A → RV + S | 5.9 ± 0.3 | 278 ± 7 |
| FIG. 5 | RV → P | P + S → RV + A | A → S | 4.9 ± 0.4 | 258 ± 9 |
| FIG. 6 | P + S → RV + A | RV → P | A → S | 6.1 ± 0.4 | 278 ± 9 |
| TM | RV → P | A → S | RV + A → P + S | 19.7 ± 1.2 | 500 ± 14 |

The triphasic waveforms according to the invention were superior and required substantially less energy as compared to the TM waveform that included no change of polarity.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments and examples disclosed, and that modifications and embodiments are intended to be included within the scope of the appended claims.

That which is claimed is:

1. A method for controlling ventricular fibrillation or tachycardia in a heart, the method comprising the steps of:

positioning a first pair of opposing electrodes and a second pair of opposing electrodes adjacent predetermined portions of the heart;

charging a storage capacitor; and delivering a series of four electrical pulses to the heart from the thus charged storage capacitor, a first electrical pulse delivered by the first pair of electrodes in a predetermined polarity, a second electrical pulse delivered by the second pair of electrodes in a predetermined polarity, a third electrical pulse delivered by the first pair of electrodes in the opposite polarity to the first pulse, and a fourth electrical pulse delivered by the second pair of electrodes in the opposite polarity to the second pulse.

2. The method according to claim 1 wherein the first and third electrical pulses define a first biphasic signal, and wherein the third electrical pulse is delivered not greater than a predetermined time after the first electrical pulse so that the defibrillation efficacy of the first biphasic signal is substantially the same as the defibrillation efficacy of a biphasic signal generated from two consecutive electrical pulses of opposite polarity.

3. The method according to claim 2 wherein the second and fourth electrical pulses define a second biphasic signal, and wherein the fourth electrical pulse is delivered not greater than a predetermined time delay after the second electrical pulse so that the defibrillation efficacy of the second biphasic signal is substantially the same as the defibrillation efficacy of a biphasic signal generated from two consecutive electrical pulses of opposite polarity.

4. The method according to claim 3 wherein the predetermined time for the both the first and second biphasic signals is about 6 ms.

5. The method according to claim 1 wherein each of the first through the fourth electrical pulses is delivered for a time period in the range of about 2 ms to 6 ms.

6. The method according to claim 1 wherein the step of positioning the first and second pairs of electrodes comprises positioning the pairs of electrodes so that each pair produces a relatively high current flow in regions of the heart where the other pair produces a relatively low current flow.

7. The method according to claim 1 wherein the step of positioning the first pair of electrodes comprises the steps of positioning a first catheter electrode in the right ventricle and a second subcutaneous patch electrode on the left thorax.

8. The method according to claim 1 wherein the step of positioning the first pair of electrodes comprises the steps of positioning a first catheter electrode in the right ventricle and a second catheter electrode in the coronary sinus.

9. The method according to claim 1 wherein the step of positioning the second pair of electrodes comprises the steps of positioning a third patch electrode on the left ventricular apex and a fourth catheter electrode in the superior vena cava.

10. The method according to claim 1 wherein the step of positioning the second pair of electrodes comprises the steps of positioning a third patch electrode on the left ventricular apex and a fourth catheter electrode in the right ventricular outflow tract.

11. A method for controlling ventricular fibrillation or tachycardia in a heart, the method comprising the steps of:

positioning a series of four electrodes adjacent predetermined portions of the heart, a first and a second electrode in opposing relation and defining a first electrode pair, and a third and a fourth electrode in opposing relation and defining a second electrode pair; and delivering a series of three electrical pulses to the heart, two of the electrical pulses delivered by the first electrode pair in a predetermined polarity and by the second electrode pair in a predetermined polarity respectively, and the other electrical pulse delivered by the first and third electrodes jointly and the second and fourth electrodes jointly in a polarity opposite the respective predetermined polarities of the two electrical pulses delivered by the first and second electrode pairs.

12. The method according to claim 11 wherein the step of delivering the electrical pulse by the first and third electrodes jointly and the second and fourth electrodes jointly is performed third in the series of three electrical pulses.

13. The method according to claim 11 wherein the step of delivering the electrical pulse by the first and third electrodes jointly and the second and fourth electrodes jointly is performed second in the series of three electrical pulses.

14. The method according to claim 11 wherein the step of delivering the electrical pulse by the first and third electrodes jointly and the second and fourth electrodes jointly is performed first in the series of three electrical pulses.

15. The method according to claim 11 further comprising the step of charging a storage capacitor; and wherein the step of delivering the series of three electrical pulses to the heart comprises delivering same from the thus charged storage capacitor.

16. The method according to claim 11 wherein the step of positioning the first and second pairs of electrodes comprises positioning the pairs of electrodes so that each pair produces a relatively high current flow in regions of the heart where the other pair produces a relatively low current flow.

17. The method according to claim 11 wherein the step of positioning the first and second electrodes comprises the steps of positioning a first catheter electrode in the right ventricle and a second subcutaneous patch electrode on the left thorax, respectively.

18. The method according to claim 11 wherein the step of positioning the first and second electrodes comprises the steps of positioning a first catheter electrode in the right ventricle and a second catheter electrode in the coronary sinus, respectively.

19. The method according to claim 11 wherein the step of positioning the third and fourth electrodes comprises the steps of positioning a third patch electrode on the left ventricular apex and a fourth catheter electrode in the superior vena cava, respectively.

20. The method according to claim 11 wherein the step of positioning the third and fourth electrodes comprises the steps of positioning a third patch electrode on the left ventricular apex and a fourth catheter electrode in the right ventricular outflow tract.

21. An apparatus for controlling ventricular fibrillation or tachycardia in a heart, said apparatus comprising:

a first pair of opposing electrodes and a second pair of opposing electrodes adapted to be positioned adjacent predetermined portions of the heart; and an electrical pulse generator electrically connected to said first and second pairs of electrodes, said electrical pulse generator comprising
a storage capacitor and means for storing an electrical charge therein, and
means for delivering a series of four electrical pulses to the heart from the charged storage capacitor, a first electrical pulse for delivery by the first pair of electrodes in a predetermined polarity, a second electrical pulse for delivery by the second pair of electrodes in a predetermined polarity, a third electrical pulse for delivery by the first pair of electrodes in the opposite polarity to the first pulse, and a fourth electrical pulse for delivery by the second pair of electrodes in the opposite polarity to the second pulse.

22. The apparatus according to claim 21 wherein said means for delivering said series of electrical pulses comprises means for controlling the duration of each pulse and the time delay between successive pulses so that a leading edge of the third pulse is delivered not greater than about 6 ms from a trailing edge of the first pulse and a leading edge of the fourth pulse is delivered not greater than about 6 ms from a trailing edge of the second pulse.

23. The apparatus according to claim 22 wherein said means for controlling the time duration of each pulse includes means for controlling the duration of each pulse within the range of about 2 ms to 6 ms.

24. The apparatus according to claim 21 further comprising an implantable housing for enclosing said electrical pulse generator.

25. The apparatus according to claim 24 further comprising a battery power supply enclosed within said implantable housing.

26. The apparatus according to claim 24 further comprising an arrhythmia detector enclosed within said implantable housing for triggering said electrical pulse generator responsive to detecting fibrillation or tachycardia of the heart.

27. An apparatus for controlling ventricular fibrillation or tachycardia in a heart, said apparatus comprising:
- a first pair of opposing electrodes and a second pair of opposing electrodes adapted to be positioned adjacent predetermined portions of the heart, said first pair of electrodes comprising first and second electrodes, said second pair of electrodes comprising third and fourth electrodes; and
- an electrical pulse generator connected to said first and second pairs of electrodes, said electrical pulse generator including means for delivering a series of three electrical pulses to the heart, two of said electrical pulses for delivery by said first electrode pair in a predetermined polarity and by said second electrode pair in a predetermined polarity respectively, and the other electrical pulse for delivery by said first and third electrodes jointly and said second and fourth electrodes jointly in a polarity opposite the respective predetermined polarities of said two electrical pulses for delivery by said first and second electrode pairs.

28. The apparatus according to claim 27 wherein said means for delivering said series of three electrical pulses comprises means for delivering said electrical pulse by said first and third electrodes jointly and said second and fourth electrodes jointly third in said series of three electrical pulses.

29. The apparatus according to claim 27 wherein said means for delivering said series of three electrical pulses comprises means for delivering said electrical pulse by said first and third electrodes jointly and said second and fourth electrodes jointly second in said series of three electrical pulses.

30. The apparatus according to claim 27 wherein said means for delivering said series of three electrical pulses comprises means for delivering said electrical pulse by said first and third electrodes jointly and said second and fourth electrodes jointly first in said series of three electrical pulses.

31. The apparatus according to claim 27 wherein said means for delivering said series of three electrical pulses includes means for controlling the time duration of each electrical pulse within the range of about 2 ms to 6 ms.

32. The apparatus according to claim 27 wherein said electrical pulse generator further comprises a storage capacitor and means for storing an electrical charge therein; and wherein said means for delivering said series of three electrical pulses comprises means for delivering same from the charged storage capacitor.

33. The apparatus according to claim 32 further comprising an implantable housing for enclosing said electrical pulse generator; and wherein said means for storing an electrical charge in said storage capacitor includes a battery power supply.

34. The apparatus according to claim 33 further comprising an arrhythmia detector enclosed within said implantable housing for triggering said electrical pulse generator responsive to detecting fibrillation or tachycardia of the heart.

* * * * *